ically balanced aqueous solution of ingredients for maintaining erythrocyte morphology, blood cell stabilizing, buffering and bacteriostatic action. The stromatolyzing reagent is a mixture of an aqueous solution of quaternary ammonium salts, a chromagen forming agent and an additive which is a non-cationic surfactant. The quaternary ammonium salts, with the additive, serve the purpose of positioning, relative to one another and a volume reference point, the lymphoid and myeloid populations. The additive also acts to prevent or to reduce the amount of protein deposit in the sensing orifices of the analyzer, which deposit tends to accumulate from the cell debris resulting from blood cell stromatolyzation.

United States Patent [19]
Carter et al.

[11] Patent Number: 4,528,274
[45] Date of Patent: Jul. 9, 1985

[54] MULTI-PURPOSE BLOOD DILUENT AND LYSING AGENT FOR DIFFERENTIAL DETERMINATION OF LYMPHOID-MYELOID POPULATION OF LEUKOCYTES

[75] Inventors: James H. Carter, Ft. Lauderdale; Stephen L. Ledis, Hialeah; Harold R. Crews; Ted Sena, both of Miami; Fred L. Larsen, Miami Lakes, all of Fla.

[73] Assignee: Coulter Electronics, Inc., Hialeah, Fla.

[21] Appl. No.: 478,960

[22] Filed: Mar. 25, 1983

Related U.S. Application Data

[63] Continuation-in-part of Ser. No. 395,530, Jul. 6, 1982, which is a continuation of Ser. No. 159,782, Jun. 16, 1980, Pat. No. 4,346,018.

[51] Int. Cl.$^3$ .................. G01N 33/48; C09K 3/00
[52] U.S. Cl. .................. 436/10; 436/17; 436/18; 436/63
[58] Field of Search .................. 436/10, 17, 18, 63

[56] References Cited

U.S. PATENT DOCUMENTS

| | | | |
|---|---|---|---|
| 3,853,465 | 12/1974 | Rush et al. | 436/16 |
| 3,874,852 | 4/1975 | Hamill | 435/17 |
| 4,099,917 | 7/1978 | Kim | 436/18 |
| 4,102,810 | 7/1978 | Armstrong | 436/17 |
| 4,185,964 | 1/1980 | Lancaster | 436/18 |
| 4,213,876 | 7/1980 | Crews et al. | 436/10 |
| 4,248,634 | 2/1981 | Forester | 436/18 |
| 4,286,963 | 9/1981 | Ledis et al. | 436/18 |
| 4,290,772 | 9/1981 | Fret | 436/18 |
| 4,297,238 | 10/1981 | Vormbrock et al. | 436/17 |
| 4,299,726 | 11/1981 | Crews et al. | 436/18 |
| 4,346,018 | 8/1982 | Carter et al. | 436/17 |
| 4,358,394 | 11/1982 | Crews et al. | 436/18 |
| 4,384,971 | 5/1983 | Carter et al. | 252/106 |
| 4,412,004 | 10/1983 | Ornstein et al. | 436/10 |
| 4,485,175 | 11/1984 | Ledis et al. | 436/17 |

FOREIGN PATENT DOCUMENTS

| | | | |
|---|---|---|---|
| 53-100298 | 9/1978 | Japan | 436/17 |
| 2077916 | 12/1981 | United Kingdom | 436/18 |

OTHER PUBLICATIONS

Nicol, D. J. et al., J. Clinical Pathology (1971) 24, p. 882.
Davis, R. E. et al., J. Med. Lab. Technol. (1969) 26, 26–30.
Barnard, D. E. et al., J. Clin. Path., 22, Suppl. Coll. Path. (1969) 3, 26–33.
Ballard, B. C. D., J. Clin. Path., 25, p. 460 (1972).
Hatch et al, Am. J. Clin. Path., 36, 220–223 (1961).
Armak, Arquad, 81–6 Bulletin.
J. M. England et al, Lancet, Mar. 1, 1975, p. 492; May 22, 1976, p. 1143.
J. M. England et al, J. Clin. Path., 27, 623 (1974).
P. A. Wycherly and M. J. O'Shea, J. Clin. Path., 31, 271 (1978).
D'Angelo et al, J. Clin. Path., 38, No. 6, 658–662.

*Primary Examiner*—Teddy S. Gron
*Attorney, Agent, or Firm*—Meredith P. Sparks; Gerald R. Hibnick

[57] ABSTRACT

A method and reagent system is described for differential determination of more that one class of leukocyte populations, using an automatic blood cell analyzer. The reagent system includes a blood diluent and stromatolyzing reagent. The blood diluent is an osmotically balanced aqueous solution of ingredients for maintaining erythrocyte morphology, blood cell stabilizing, buffering and bacteriostatic action. The stromatolyzing reagent is a mixture of an aqueous solution of quaternary ammonium salts, a chromagen forming agent and an additive which is a non-cationic surfactant. The quaternary ammonium salts, with the additive, serve the purpose of positioning, relative to one another and a volume reference point, the lymphoid and myeloid populations. The additive also acts to prevent or to reduce the amount of protein deposit in the sensing orifices of the analyzer, which deposit tends to accumulate from the cell debris resulting from blood cell stromatolyzation.

24 Claims, 4 Drawing Figures

MULTI-PURPOSE BLOOD DILUENT AND LYSING AGENT FOR DIFFERENTIAL DETERMINATION OF LYMPHOID-MYELOID POPULATION OF LEUKOCYTES

This application is a continuation-in-part of pending application, Ser. No. 395,530, filed July 6, 1982, for Multi-Purpose Blood Diluent and Lysing Agent for Differential Determination of Lymphoid-Myeloid Populations of Leukocytes, the latter application being a continuation of Ser. No. 159,782, filed June 16, 1980, which has now issued as U.S. Pat. No. 4,346,018.

BACKGROUND OF THE INVENTION

This invention concerns a reagent system for volume differentiation of at least two populations of leukocytes including a blood diluent especially suitable for use in electronic enumeration and sizing of blood cells, determination of hemoglobin and their collective indices and platelet parameters in a single blood cell sample by means of suitable electronic instrumentation, and a stromatolyzing reagent for use therewith.

The diluent comprises a stable water solution of chemical salts providing an electrolytic solution capable of conducting current to which a blood sample can be added so as to dilute the red blood cells, white blood cells, platelets and other blood components and enable the desired parameters of these blood components to be measured, counted and evaluated.

It is a common medical diagnostic procedure to analyze and test a blood sample of a patient in order to make certain classic determinations with respect to the blood sample. This procedure is an important tool for the physician. Six characteristically important parameters are referred to as red blood cell count (RBC), the hematocrit (HCT), the hemoglobin (Hgb), the mean corpuscular volume (MCV), the mean corpuscular hemoglobin (MCH), and the mean corpuscular hemoglobin concentration (MCHC). A seventh important determination is white blood cell count (WBC).

Much effort has been devoted to the development of satisfactorily automated leukocyte differential systems. However, a need exists for reagent systems which will be easily adaptable to automatic blood counting instruments. In particular, it is desirable to develop reagents and methods for use with the COULTER COUNTER Model S Plus series of automated blood cell counters, manufactured by Coulter Electronics, Inc. of Hialeah, Fla., which will enable the cell volume data accumulated on a COULTER CHANNELYZER to discriminate: (1) a lymphoid and a myeloid population, as described in U.S. Pat. No. 4,346,018, and (2) a lymphocyte, monocyte and granulocyte population, as described in copending U.S. application Ser. No. 454,926, now U.S. Pat. No. 4,485,175. Such data are useful as a screening tool for spotting abnormal leukocyte ratios. Abnormal situations flagged out by this method give information of diagnostic significance, and for further study. COULTER, COULTER COUNTER and CHANNELYZER are registered trademarks of Coulter Electronics, Inc.

Separation of normal human leukocytes by volume distribution was first documented by Gauthier and colleagues, (Gauthier, J., Harel, P., Belanger, C. and Fraysse, J., Can. Med. Assoc. J. 97, 793, (1967) and Van Dilla and colleagues, (Van Dilla, M. A., Fulwyler, M. J. and Boone, I. U., Proc. Soc. Esp. Biol. Med. 125, 367, in 1967) as a possible clinical diagnostic method utilizing the principle of counting and sizing developed by Wallace H. Coulter and employed in COULTER COUNTER instruments. These methods were based on the fundamental property of all living cells to regulate their cell volume by genetic code information. Each type of cell in the circulating blood has its own characteristic volume ranging from as small as 3 fL for platelets to more than 450 fL for polymorphonuclear cells (fL designates $1 \times 10^{-15}$ liters, a femtoliter). Advanced COULTER COUNTER instruments have been designed to make use of this volume differential for the purposes of counting and determining the size distribution of cell components and to detect and monitor pathological states.

Electrical sizing of particles in suspension by a COULTER COUNTER type instrument has been previously described and documented by many clinical hematology investigators. It is well known that the form and size of the electrical pulse generated by a particle passing through a defined electrical field is influenced by several factors including size, shape and conductance of the particles being counted. In blood cell preparations diluted in an isotonic salt solution, conductivity of the cell membrane is far lower than conductivity of the diluent, and therefore, blood cells may be considered to be electrically non-conducting for practical considerations.

Erythrocytes and the lymphoid leukocytes unfortunately overlap considerably in cell size, and it is not possible to count one in the presence of the other by size discrimination alone. Traditional practice involves the use of a strong reagent that stromatolyses the erythrocytes, reducing them to very small particles or causing membrane solubilization, and at the same time strips the cytoplasm from the leukocytes, leaving only the resistant nuclei to be counted. Since original cell volume is drastically affected and reduced to a minimum, only a single population is visible by size distribution analysis.

The COULTER COUNTER Model S Plus automated blood cell counter is designed to dilute a sample of whole blood in an isotonic diluent, add a stromatolysing reagent, and then begin counting after a few seconds. Data typically are collected for a very few seconds for erythrocytes, leukocytes and platelets; however, an increase in count cycles of a few seconds each can be invoked automatically by the instrument system to achieve need statistical accuracy. Thus, a diluent-lysing reagent system for measuring more than one population of leukocytes must provide erythrocyte lysing kinetics sufficiently rapid to effect complete stromatolysation of the erythrocytes during the lysing period. Changes in leukocyte volume must be minimal during the data collection step and ideally should be stable for several minutes. The reagent system must also preserve the integrity of the erythrocyte and platelet number and size distribution, the hemoglobin absorbance curve and the total leukocyte count. Finger stick bloods should be stable when pre-diluted in the isotonic diluent for at least two hours.

To achieve an analysis of the relative populations of lymphoid and myeloid cells in the blood, the leukocyte volume histogram must show cleanly separated lymphoid and myeloid peaks, with little erythrocyte debris, allowing valleys very close to the baseline. Integration of each peak will give the relative populations of the lymphoid and myeloid cells. The lymphoid peak has been demonstrated to contain lymphocytes and variant lymphocytes, while the myeloid peak contains polymorphonuclear cells, bands, monocytes, eosinophils, basophils and other abnormal cells.

In U.S. Pat. No. 3,874,852 (1975) to Coulter Diagnostics, Inc., a reagent formula is included for a composition containing one quaternary ammonium salt detergent and potassium cyanide to be employed as a lysing and chromagen-forming reagent for obtaining a total leukocyte count, without regard for subpopulations, and hemoglobin determination in the COULTER COUNTER Model S. Further investigations was required to use a plurality of quaternary ammonium salts as lysing agents for obtaining the two-population leukocyte count.

In U.S. Pat. No. 4,286,963 (1981) to Coulter Electronics, Inc. a lytic diluent for the rapid lysing of red blood cells in whole blood for making a differential determination of lymphoid/myeloid populations of leukocytes, and also measuring hemoglobin by chromagen formation, contains a mixture of an aqueous saline solution of at least one quaternary ammonium salt having surface acting properties, and certain additives such as 2-phenoxyethanol.

It is known that two volume distribution analysis is difficult because, with many reagent systems, the two populations rapidly move into one so that there is not enough time within which to make the computations for analysis.

In U.S. patent application, Ser. No. 454,926, filed Jan. 3, 1983, now U.S. Pat. No. 4,485,175, a method and reagent system is described for three-volume differential determination of lymphocyte, monocyte and granulocyte populations of leukocytes.

In U.S. patent application, Ser. No. 295,933, filed Aug. 24, 1981, now U.S. Pat. No. 4,384,971, issued May 24, 1983, there is described a cleansing composition for electronic particle counting apparatus, and method for its use. This composition includes a non-hemolytic polyoxyethylated alkylphenol detergent, dimethylolurea and 1-hydroxypyridine-2-thione which is adjusted to a predetermined osmolality.

SUMMARY OF THE INVENTION

The present invention relates to a method for subjecting a whole blood sample to a reagent system to achieve at least a volumetric differentiation of more than one class of leukocyte populations. More particularly, it relates to a diluent and stromatolysing reagent which includes an additive which is a non-cationic surfactant.

The reagent system employed includes a multi-purpose isotonic blood diluent that comprises a mixture of organic buffering means, cell membrane stabilizing means, and a germicidal means, the end volume concentration of which serves to control the lytic kinetics of the stromatolysing reagent upon the leukocytes and achieve a differential volume reduction, while stabilizing the traditional hemogram parameters.

The stromatolysing reagent best suited to this inventive method is a mixture of an aqueous solution of quaternary ammonium salts having surface active properties and a non-cationic surfactant additive in a volume concentration range that is effective to give the desired leukocyte volume histograms. The stromatolysing reagent is hypotonic and therefore tends to combat the shrinkage of the myeloid cells, such shrinkage being well known in the art. Data are presented using standard COULTER COUNTER blood cell analyzing equipment in conjunction with a COULTER CHANNELYZER instrument and an X-Y plotter. Ancillary calculating and data handling devices are desirable for complete automation, but are not essential to performance of the measurements.

In the preferred commercial embodiment utilizing this invention an alkali metal cyanide is added as the chromagen-forming agent. Other chromagen-forming agents, such as Drabkin's reagent, which contains potassium ferricyanide, potassium cyanide and sodium bicarbonate also may be used.

The preferred non-cationic surfactants which are useful as additives include the nonionic surfactants, such as the polyoxyethylated alkylphenols, or the polyethylene glycol phenol ethers; and the anionic alkali metal salt of a $C_{10}$–$C_{14}$ alkyl sulfate. The additive serves the dual purpose of: (1) allowing for the manufacture of a lysing agent that will accurately position the lymphocyte and myeloid populations of the instrument, and (2) also acts to prevent or to reduce the amount of protein deposit in the sensing orifices of the instrument which tends to accumulate from the cell debris resulting from blood cell stromatolysation.

BRIEF DESCRIPTION OF THE DRAWINGS

In the figures, the X-axis is femtoliters and the Y-axis is normalized cell count.

FIG. 1 comparatively shows a pair of two-population histograms developed from the same normal blood using a stromatolysing reagent having two different amounts of the same additive, a polyoxyethylated alkylphenol nonionic surfactant, but the same quantity of two quaternary ammonium salts, the amount of one salt being different from the other;

FIG. 2 comparatively shows a pair of two-population histograms developed from the same normal blood using a stromatolysing reagent having two different amounts of the same additive as in FIG. 1, and significantly different amounts of the same two quaternary ammonium salts than as in FIG. 1;

FIG. 3 comparatively shows a trio of two-population histogram developed from the same normal blood each using a stromatolysing reagent having the same preferred combination of amounts of the two quaternary ammonium salts, but two having different additives and one having no additive; and FIG. 4 comparatively shows a pair of three-population histograms developed from the same normal blood using a stromatolysing reagent having preferred amounts of the two quaternary ammonium salts, but two different amounts of the same nonionic surfactant.

DETAILED DESCRIPTION OF THE INVENTION

Figure 1:
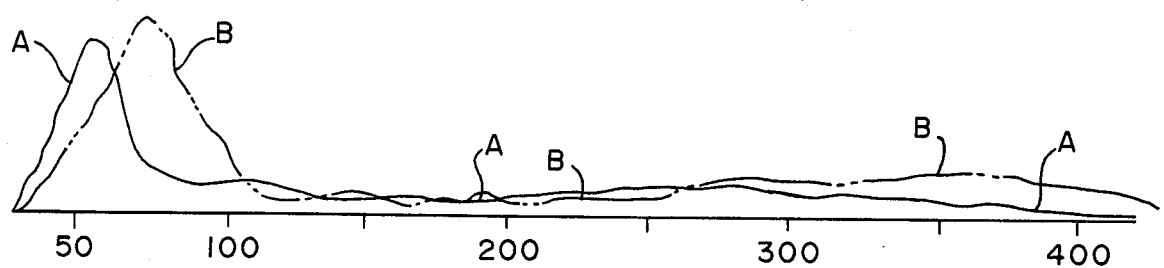
In FIGS. 1, 2 and 3 the population at the left is lymphoid, and at the right is myeloid.

The introduction of high speed automated hematology instruments such as the COULTER COUNTER Model S as described in U.S. Pat. No. 3,549,994 resulted in a need for a high speed erythrocyte stromatolysing reagent which gives a clear, stable, reproducible solution. In such an instrument, blood is mixed with a conventional diluent, to provide a first dilution, and then mixed with a lysing agent, to provide a second dilution. The mixture remains in the lysing chamber for a short but sufficient amount of time for the erythrocytes or red blood cells to be disintegrated (stromatolysed) and release their hemoglobin. The lysing agent also converts the hemoglobin to a chromagen suitable for measurement. The resulting suspension is passed through sensing apertures in a leukocyte, counting bath, wherein the leukocytes or white blood cells are counted and sized electronically. Inasmuch as the ratio of erythrocytes to leukocytes in normal blood is the vicinity of 1000:1, the erythrocytes must be reduced rapidly to very small fragments, to avoid interference with leukocyte counting. At the same time, the leukocytes must not be destroyed, even though they will shrink in size to a greater or lesser degree.

A quaternary ammonium salt having surface active properties advantageously is employed as the stromatolysing agent in the COULTER blood cell analyzer, with the virtually instantaneous destruction of erythrocytes to a level avoiding interference with leukocyte sizing and counting. The quaternary ammonium salt is included in aqueous solution in a concentration within the overall range of about 0.5 to 10 percent, and preferably about 1 to 5 percent by weight of the solution, and is mixed with blood previously diluted with a diluent, in a ratio of about 1:10 lysing agent volume to diluted sample volume in the counting bath. It will be understood that a different strength lysing agent may be employed where the initial dilution of the blood sample differs from that described above, in order to provide the same ultimate concentration of reactive lysing agent, or ratio of lysing reagent to whole blood present in the counting bath.

When making a two-volume separation of lueko-cytes, according to the method of U.S. Pat. No. 4,346,018, it had been observed that the lymphoid-myeloid histograms obtained after lysis on the COULTER COUNTER S Plus instrument consisted of a lymphoid peak at about 50 to 100 fL, and a myeloid peak, containing monocytes and granulocytes (eosinophils and neutrophils) in the volume range of 100 to 450 fL.

The specific quaternary ammonium compound and its concentration are selected to provide the necessary hemolytic activity and solubility of the quaternary ammonium compound. In general, with increasing number of carbon atoms, the solubility of the compound decreases, and with increasing number of carbon atoms in the long chain, the hemolytic activity increases.

The long chain quaternary ammonium compounds useful for their strong lytic action on erythrocytes are commercial materials derived from natural products which may vary somewhat from time to time in their lysing strength, due particularly to their composition with respect to the length of the carbon chain attached to the nitrogen atom. The differential determination of two or more volumes of leukocytes, on the other hand is very sensitive to the purity or strength of the lysing agent, and a reliable separation into at least two volumes of leukocytes can be difficult to attain with the available commercial products sold on the market.

We have now discovered the unexpected result that the addition of a non-cationic surfactant (either non-ionic or anionic) which alone has only minor hemolytic effect, show a synergistic interaction with the quaternary ammonium salts. Thus, moderation or a slowing down of the kinetics of the reaction to a point where reliable measurement can be taken is dependent upon the concentrations and relative ratios of both quaternary ammonium salts and the non-cationic surfactant, while still preserving the total lysing effect of the reagent. Addition of the non-cationic surfactant to a solution of the quaternary ammonium salts appears to modify the lysing rate, changing the lymphocyte volume population only slightly, but changing the myeloid volume population by a significant amount. Careful selection of the concentrations of the quaternary ammonium salts and of the non-cationic surfactant avoids excessive shrinkage of the lymphoid population, resulting in fewer "incomplete" computations. Variations in the quantities of activity of the commercial quaternary ammonium salts can easily be offset by varying the concentration of the additive agent. It is therefore more practical to control the effect of the lytic reagent by varying the concentrations of the non-cationic surfactant along with minor changes in the concentration of the quaternary ammonium salts, than by attempting to obtain precise control by modifying the content and concentration of the quaternary ammonium salts alone.

Changes in commercial products in terms of purity or concentration from lot to lot would require the use of a different concentrations of each quaternary ammonium salt, or mixtures thereof, for each lot used in order for the lysing formula to achieve the same end results with the instrument system. The cell size distribution measurement is determined by the instrument system by means of a predetermined time "window" in the counting cycle, during which the cell lysing process is nearly complete and cell volume changes are proceeding slowly enough for the instrument to measure numbers and relative volumes of the now differentiated leukocytes. The cells must also fall within the volume range of 45 to 99 fL for lymphoids and 100 to 450 fL for myeloids. Thus, the lysing reaction must be made to occur rapidly enough so that the cell differentiation changes are substantially complete when the time "window" opens and data are collected. Since the timing parameters are a part of the overall operational program of the instrument system, these are essentially predetermined and fixed by the manufacturer at the time of sale. Any adjustments in data positioning necessary are therefore more readily made by adjustment of the lysing agent formulation. Unexpectedly, it has been found that the "fit" of the cell population data in the measurement range "window" of the instrument system can be attained readily by a suitable amount of an additive which is a non-cationic surfactant to the stromatolysing agent in order to regulate the kinetics of its action. Thus fine-tuning of the equipment is best accomplished by varying the concentration of the additive agent in the stromatolysing reagent rather than by changes in the equipment. The improvement of this invention accordingly relates to the ability to position, relative to one another and a volume reference point, the lymphoid and myeloid populations within the time constraints of the instrument. This result is accomplished by more sensitive control of the rate of reaction of the stromatolysing agent, by using an additive which is a non-cationic surfactant.

This additive also serves a dual purpose in that it also acts to prevent or to reduce the amount of protein deposit in the sensing orifices of the instrument which tends to accumulate from the cell debris resulting from the blood cell stromatolysation. Satisfactory performance of any of the countings and sizings functions of automated hematology instruments using electronic pulses generated in accordance with the Coulter Principle is dependent on maintaining clean and unimpeded fluid pathways, especially in and near the sensing apertures. Due to the small size of the aperture and the inaccessability of much of the fluid path, this self-cleaning feature assumes great importance in such equipment.

Studies made of the optimum concentrations of the $C_{14}$ lysing reagent for COULTER COUNTER Model S Plus II for counting two volumes of leukocytes is about 12–14 g/L. At these concentrations the lymphoid distribution width is quite narrow, and the myeloid distribution is positioned to the right side of the CHANNELYZER plot. The concentration of $C_{12}$ quat necessary for correct placement of the lymphocyte populations for this concentration of $C_{14}$ is somewhat more flexible, but the optimum concentration is about 30–40 g/L of the active agent. The lymphoid distribution will then fit within the 45–99 fL volume region and have modal volumes between 65–75 fL.

The myeloid distribution moves to the right (larger apparent volumes) in the presence of low concentrations of $C_{14}$ and high concentrations of $C_{12}$.

The myeloid distributions are shifted to the left (smaller apparent volumes) when exposed to higher concentrations of $C_{14}$ and less $C_{12}$.

The effect of using as addition agent the nonionic polyoxyethylated alkylphenol surfactant or the anionic surfactant sodium lauryl sulfate is similar. Both compounds move the lymphoid and myeloid populations proportionately to the right (larger apparent volumes). Sodium lauryl sulfate is more potent in this regard.

Studies using dimethylethylhexadecylammonium bromide in the lysing agent show comparable results.

The significance of these findings relates to the ability to position, relative to one another and a volume reference point, the lymphoid and myeloid populations within the time constraints of the instrument. By the use of appropriate concentrations of essentially non-hemolytic surfactants, these distributions can be altered to achieve the desired apparent volume for accomodating the engineering aspects of the blood cell analyzing equipment.

As disclosed in U.S. patent application Ser. No. 454,926, filed Jan. 3, 1983, now U.S. Pat. No. 4,485,175, when making a three-volume separation of leukocytes, it was discovered and determined by experimentation that the lymphocytes and monocytes are more sensitive than the granulocytes to the lytic agents usually employed. By modifying the kinetics of the lytic method in the COULTER COULTER S Plus instrument to allow a more mild exposure of the white cells in the blood sample to the lyse reagent, the granulocytes were less "shocked", i.e. subject to a lower or low gradient of lytic shock, and thereby not reduced in size to the extent caused by prior reagent systems and methods. This is accomplished by treating the diluted blood sample with the stromatolysing reagent less rapidly, and when the stromatolysing reagent is in lower concentration than is routinely the case. However, approximately the same amount of lyse reagent is needed in order to ensure complete stromatolysation of the red blood cells. By modification of the kinetics of the method, the lymphocytes are reduced in volume to 50 to 100 fL, the monocytes are reduced to 100 to 150 fL and the granulocytes demonstrate a volume range of 180 to 450 fL. Consequently, the granulocyte population no longer overlaps the monocyte population and these populations can be enumerated separately. The resulting data must be obtained within a time frame during which time three distinct populations are present.

This was the first time that it had been learned how to control the kinetics of the action so as to obtain this important result. In the past, the emphasis has been on the virtually instantaneous destruction of the red blood cells to a level avoiding interference with leukocyte estimation. Herein, the emphasis is on discerning the differential volumes of the individual classes of white cells which, unlike the red blood cells, vary in many ways with respect to morphology and the presence of various nuclear forms, volume, as well as function, in health and with disease.

A simplified general description of the blood cell analyzer instruments which utilize the Coulter Principle of operation is that they include two fluid vessels or chambers, each containing a conductive electrolyte solution. At least two electrodes having opposite polarity are immersed in the electrolyte solution, with each fluid compartment having one of the electrodes disposed therein. A sample of the electrolyte solution, having the blood cells suspended therein, is passed through a constricted fluid path or orifice interposed between the two fluid compartments. Although the constricted path can take different forms, in each device such path defines a sensing zone wherein the presence or absence of a particle gives rise to a detectable change in electrical characteristics of the path. For example, relatively poorly conductive blood cells passing through this path displace a volume of electrolyte solution equal to the cell volume, causing a voltage drop by increasing the path impedance. The resistance pulses defined by the drops in voltage are used for particle counting and particle volume determination.

The COULTER COUNTER Model S Plus series of automated blood cell counters are designed to dilute a sample of whole blood in an isotonic electrically conductive diluent, add a lysing agent, and shortly thereafter begin counting. The diluent-lysing system must provide erythrocyte lysing kinetics sufficiently rapid to effect complete stromatolysation of the red blood cells (erythrocytes) during the lysing period. During this time period, the cytoplasm is rapidly removed from the leukocytes, ordinarily leaving only a single volume of the lyse-resistant nuclei to be counted. Since original cell volume is drastically affected and reduced to a minimum, only a single leukocyte population may be discerned. It is evident that the data displayed is related both to the time cycle program provided for the instrument and to the kinetics of the lysing reaction, as well as to the initial engineering design parameters of the equipment at the time it is marketed. By moderating the speed with which the lysing takes place in an appropriate manner under predetermined conditions, the display may show more than one volume of leukocytes, as is described with particularity in copending application Ser. No. 454,925, filed Jan. 3, 1983, U.S. Pat. No. 4,485,175, and in U.S. Pat. No. 4,346,018.

A preferred class of the non-cationic surfactants useful for the purpose of this invention includes the nonionic polyoxyethylated alkylphenols which are manufactured by methods known in the art by reaction of alkylated phenols with an excess of ethylene oxide to form alkyl aryl ethers of polyethylene, for example, by the following reaction:

$$RC_6H_4OH + x(CH_2CH_2O) \rightarrow RC_6H_4O(CH_2CH_2O)_{x-1}CH_2CH_2OH$$

where R is an alkyl group having 8 to 10 carbon atoms, and x is an integer 8 to 30.

An especially preferred member of this group is the compound where R=9 and x=30. The compound has the following product characteristics:

| | |
|---|---|
| Appearance | clear, almost water-white liquid |
| 1% solution | clear and colorless |
| solubility in water | readily soluble, even in cold water |
| pH of 1% solution | neutral |
| stability | stable to acids, alkalis and metallic ions |
| cloud point | clear at 212° C. |

Figure 2:
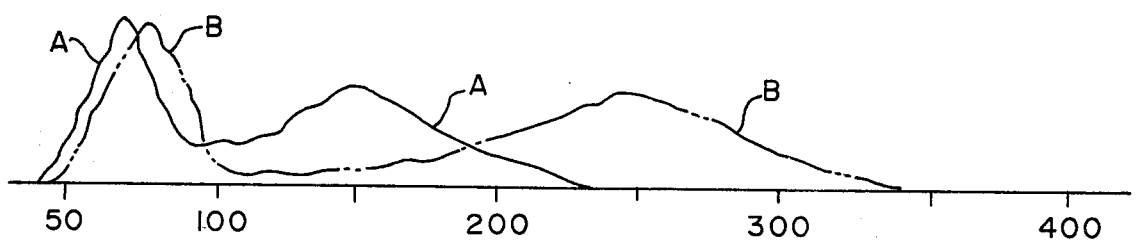
Figure 4:
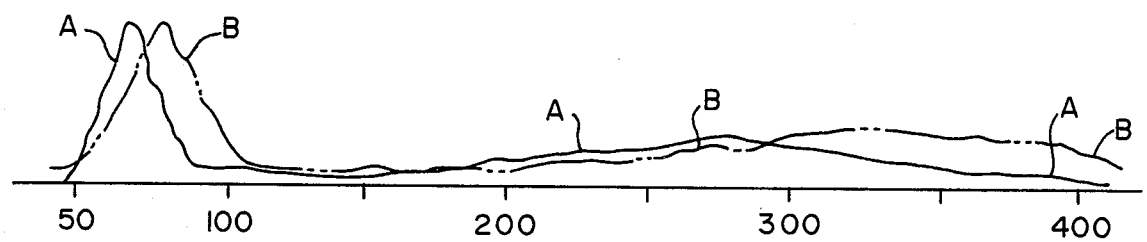
In FIG. 4, the three populations, left to right respectively, are lymphocyte, mononuclear and granulocyte.

Results from the use of this compound are shown in histograms or traces B in FIGS. 1, 2, and 4.

The following nonionic surfactants can be used to obtain comparable results to that shown in histograms B in FIGS. 1, 2, 3 and 4:

Alkylphenoxypoly(ethyleneoxy)ethanol where alkyl=-normal or isomeric $C_8$, $C_9$, $C_{10}$, $C_{12}$ and poly=8 to 30 moles of ethyleneoxy;

Dialkylphenolpoly(ethyleneoxy)ethanol, where alkyl=$C_8$, $C_9$, and poly=8 to 30 moles of ethyleneoxy alkyl aryl polyglycol ether, where alkyl=$C_8$, $C_9$, and poly=8 to 30 moles of ethyleneoxy ethoxylated phenol, with no alkyl chain.

Condensates of propylene glycol and propylene oxide with ethylene oxide giving a poly(oxypropylene)-poly(oxyethylene)ethanol with poly(oxypropylene)=15 to 45 moles and poly(oxyethylene)=120 to 180 moles.

Figure 3:
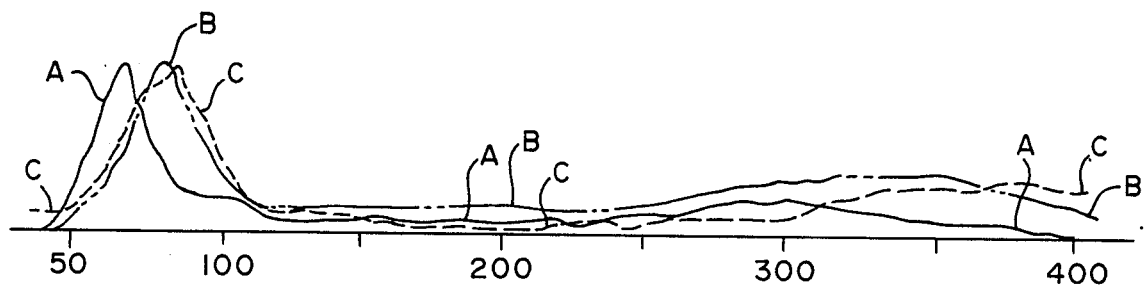

The following anionic surfactants can be used to obtain results comparable to sodium lauryl sulfate shown in histogram C of FIG. 3:

Alkyl sulfonic acid salts (salt=Na, K, $NH_4$; alkyl=octyl to octadecyl);
Alpha-olefin sulfonic acid salts (salt=Na, K, $NH_4$; alkenyl=$C_{12}$-$C_{18}$);
Alkyl aryl sulfonic acid salts (salt=Na, K, $NH_4$; aryl=-benzene, xylene, toluene);
Alkyl diaryl sulfonic acid salts (salt=Na, K, $NH_4$; aryl=benzene, xylene, toluene);
Sulfosuccinates, Na, K or $NH_4$;
Alkyl and dialkyl sulfosuccinates;
Alkyl phosphates;
Branched alkyl sulfates (e.g. 2-ethylhexyl sulfate);
Diethanolamine alkyl sulfate;
Alkyl ether sulfonates (e.g. sodium lauryl ether sulfonate) with 1 to 12 moles of ethylene oxide;
Alkyl naphthalene sulfonate (e.g. lauryl naphthalene sulfonate);
Nonylphenoxypoly(ethyleneoxy)ethanol (Na or $NH_4$ sulfate);
Alkoxylated arylphenol phosphate (K, Na);
Alkylphenoxypoly(ethyleneoxy)ethanol sulfate salts (K, Na).

The above compositions are sold in commerce under a number of trademarks.

Preferably, the method of this invention uses in combination:

(A) A multi-purpose isotonically balanced diluent comprising for example an aqueous solution of:
 1. organic buffering means;
 2. cell membrane stabilizing means; and
 3. germicidal means; said diluent having a predetermined pH and osmolality; and (B) a lysing agent which is an aqueous solution of quaternary ammonium salts having surface active properties.

The quaternary ammonium salts have the formula:

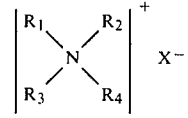

where $R_1$ is a long chain alkyl radical having 10 to 18 carbon atoms; $R_2$, $R_3$, $R_4$ are short chain alkyl radicals having 1 to 6 carbon atoms and $X^-$ is a salt forming radical such as $Cl^-$, $Br^-$, $PO_4^{-3}$ and $CH_3SO_4^-$. In the more useful combinations, the long chain alkyl has 12 to 16 carbon atoms, the short chains are methyl or ethyl, and $X^-$ is chloride or bromide.

The preferred lysing agent employs a combination of dodecyltrimethylammonium chloride, with tetradecyltrimethylammonium bromide. Other quaternary ammonium salts that give effective results include hexadecyltrimethylammonium bromide or hexadecyldimethylethylammonium bromide in combination with dodecyltrimethylammonium chloride.

To form a suitable chromagen for hemoglobin determination, as is desired for operation of a COULTER COUNTER Model S Plus instrument, there can also be provided an alkali metal cyanide, such as potassium cyanide. Other chromagen-forming agents also can be employed.

PRIOR ART EXAMPLE

Following the recommended directions which are now public knowledge for volume and flow adjustments of COULTER COUNTER Model S Plus, in order to produce two-volume (lymphoid-myeloid) populations of leukocytes, the following ingredients are employed in the concentrations indicated:

| DILUENT U.S. Pat. No. 4,346,018 (col. 3, line 55) | CONCENTRATION PREFERRED | CONCENTRATION RANGE |
|---|---|---|
| 1. Procaine hydrochloride | 0.11 g/L | 0.05 to 0.25 g/L |
| 2. N—(2-acetamido)iminodiacetic acid (ADA) | 1.40 g/L | 1.0 to 2.5 g/L |
| 3. Dimethylolurea | 1.00 g/L | 0.5 to 2.5 g/L |
| 4. sodium hydroxide | 0.50 g/1 | |
| 5. sodium sulfate, anhydrous | 0.72 g/L | |
| 6. sodium chloride | 4.50 g/L | |
| 7. water | sufficient for 1 liter | |

Experimentation has verified that the amounts of the two quaternary ammonium salts and the non-cationic surfactant additive can lie in relatively wide ranges, but that the amounts of these three components are interdependent. Yet also, within certain practical limits, the amounts of any two of these three variables can be chosen at will, with the amount of the third component then becoming defined rather narrowly. Although extreme limits of each range might work under some conditions with some blood samples, practical, commercially useful, ranges for these components are as follows:

dodecyltrimethylammonium chloride 10 to 55 g/L;

tetradecyltrimethylammonium bromide 9 to 20 g/L;
polyoxyethylated alkylphenol 4 to 20 mL/L or polyethylene glycol p-isoalkylphenyl ether 4 to 20 mL/L, or sodium lauryl sulfate 0.5 to 5 g/L;
or mixtures of two or more of these non-cationic surfactants in corresponding amounts to fit within the stated ranges of effectiveness.

EXAMPLE I

Using the same concentration of ingredients for the diluent as in the Prior Art Example, but changing the concentration of the ingredients in the lysing reagent to the amounts shown below, the results are shown in tracing A of FIG. 1 using a COULTER COUNTER Model S Plus II instrument.

| LYSING AGENT | CONCENTRATION |
| --- | --- |
| 1. Dodecyltrimethylammonium chloride | 55 g/L |
| 2. Tetradecyltrimethylammonium bromide | 9 g/L |
| 3. Potassium cyanide | 300 mg/L |
| 4. Water | sufficient for 1 liter |

When 12 mL/L of the nonionic polyoxyethylated alkylphenol surfactant described above is added to the above formula, the results are as shown on tracing B of FIG. 1.

EXAMPLE II

Using the same concentration of ingredients for the diluent as in the Prior Art Example, but changing the concentration of the ingredients in the lysing reagent to the amounts shown below, the results are shown in tracing A of FIG. 2 using a COULTER COUNTER Model S Plus II instrument:

| LYSING AGENT | CONCENTRATION |
| --- | --- |
| 1. Dodecyltrimethylammonium chloride | 10 g/L |
| 2. Tetradecyltrimethylammonium bromide | 20 g/L |
| 3. Potassium cyanide | 300 mg/L |
| 4. Water | sufficient for 1 liter |

When 8 mL/L of the nonionic polyoxyethylated alkylphenol surfactant described above is added to the above formula, the results are as shown on tracing B of FIG. 2.

EXAMPLE III

Using the same concentration of ingredients for the diluent as in the Prior Art Example, but changing the concentration of the ingredients in the lysing reagent to the amounts shown below, the results are shown in tracing A of FIG. 3 using a COULTER COUNTER Model S Plus II instrument:

| LYSING AGENT | CONCENTRATION |
| --- | --- |
| 1. Dodecyltrimethylammonium chloride | 35 g/L |
| 2. Tetradecyltrimethylammonium bromide | 13 g/L |
| 3. Potassium cyanide | 300 mg/L |
| 4. Water | sufficient for 1 liter |

When 8 mL/L of a polyethylene glycol p-isoalkylphenyl ether is added to the above formula, the results are as shown on tracing B of FIG. 3. Addition of 1.25 g/L of the anionic surfactent sodium lauryl sulfate gives tracing C of FIG. 3.

For ease of interpreting FIG. 3, not shown is a histogram representing the preferred mixture of the two quats $C_{12}$ and $C_{14}$ with 8 mL/L of the polyoxyethylated alkylphenol. Such histogram would appear most like histogram or tracing B in FIG. 3.

EXAMPLE IV

Using the same concentration of ingredients for the diluent as in the Prior Art Example, but with the following formulation of ingredients for the lysing agent and doubling the volume of the lysing agent, a three-population histogram was obtained using a COULTER COUNTER Model S Plus II instrument and following the procedures of U.S. patent application Ser. No. 452,926, filed Jan. 3, 1983:

| LYSING AGENT | CONCENTRATION |
| --- | --- |
| 1. Dodecyltrimethylammonium chloride | 18.8 g/L |
| 2. Tetradecyltrimethylammonium bromide | 6.5 g/L |
| 3. Potassium cyanide | 150 mg/L |
| 4. Water | sufficient for 1 liter |

The results are as shown in the tracing A of FIG. 4.

When 3 mL/L of the nonionic polyoxyethylated alkylphenol surfactant described above is added to the above formula, the results are as shown on tracing B of FIG. 4.

In each of the Examples I to IV, the tracing A contains no additive and, for that reason, those lysing agents will not yield cell populations (neither two nor three populations) of leukocytes which are suitably positioned for appropriate discernment or differentiation by the automated cell analyzer. Each of these histograms fail in at least one of the criteria of properly positioned cell populations, a well defined valley at the right side of the lymphoids (lymphocytes in FIG. 4), or proper population distribution width. To the contrary, all other of the produced histograms provide instrument useful differential data. This is true even though FIGS. 1 and 2 were generated by near end limits of the amounts of the quaternary ammonium salts.

While certain representative embodiments and details have been shown for the purpose of illustrating the invention, various changes and modifications can be made therein without departing from the scope of the invention as defined in the appended claims.

We claim:

1. A stromatolysing reagent for use in the determination of at least two leukocyte populations in blood, two such populations being lymphoid and myeloid, the blood being processed through a blood cell analyzer using the Coulter Principle of operation, which employs a leukocyte sensing zone, the blood having been first diluted with an electrically conductive isotonically balanced diluent, wherein said stromatolysing reagent comprises an aqueous solution of at least two quaternary ammonium salts having surface active properties and an additive which is at least one non-cationic surfactant, said salts and additive being present in sufficient amounts for positioning said leukocyte populations relative to one another and relative to a blood cell volume reference point, within the time constraints of said blood cell analyzer.

2. The stromatolysing reagent of claim 1 wherein said non-cationic surfactant additive is a nonionic polyoxyethylated alkylphenol.

3. The stromatolysing reagent of claim 2 wherein said additive has the following product characteristics:

| | |
|---|---|
| Appearance | clear, almost water-white liquid |
| 1% solution | clear and colorless |
| solubility in water | readily soluble, even in cold water |
| pH of 1% solution | neutral |
| stability | stable to acids, alkalis and metallic ions |
| cloud point | clear at 212° C. |

4. The stromatolysing reagent of claim 1 wherein the quaternary ammonium salts are those with $C_{12}$ and $C_{14}$, alkyl radicals which have useful ranges of approximately 10 to 55 g/L and 9 to 20 g/L, respectively, with said additive having a useful range of approximately 4 to 20 mL/L; such that the selection of any two of these three components anywhere within their ranges will provide a useful reagent when the amount of the third component is properly selected within its range.

5. The stromatolysing reagent of claim 4 wherein said salts are dodecyltrimethylammonium chloride and tetradecyltrimethylammonium bromide, and said additive is selected from the group consisting of:
  1. Polyoxyethylated alkylphenols,
  2. Poly(oxypropylene)poly(oxyethylene)condensates, and
  3. Polyethylene glycol p-isoalkylphenyl ethers.

6. The stromatolysing reagent of claim 1 wherein the quaternary ammonium salts are those with $C_{12}$ and $C_{14}$, alkyl radicals which have useful ranges of approximately 10 to 55 g/L and 9 to 20 g/L, respectively, with said additive having a useful range of approximately 0.5 to 5 ml/L and being an alkali metal salt of a $C_{10}$–$C_{18}$ alkyl sulfate; such that the selection of any two of these three components anywhere within their ranges will provide a useful reagent when the amount of the third component is properly selected within its range.

7. The stromatolysing reagent of claim 6 where said salts are dodecyltrimethylammonium chloride and tetradecyltrimethylammonium bromide.

8. The stromatolysing reagent of claim 1 wherein said non-cationic surfactant additive is a poly(oxypropylene)polyoxyethylene)condensate.

9. The stromatolysing reagent of claim 1 wherein said non-cationic surfactant additive is a polyethylene glycol p-isoalkylphenyl ether.

10. The stromatolysing reagent of claim 1 wherein said non-cationic surfactant additive is an alkali metal salt of a $C_{10}$–$C_{18}$ alkyl sulfate.

11. The stromatolysing reagent of claim 1 which includes the following three ingredients in approximately the concentrations indicated:
  1. Tetradecyltrimethylammonium bromide: 9 g/L
  2. Dodecyltrimethylammonium chloride: 55 g/L
  3. Polyoxyethylated alkylphenol: 12 mL/L.

12. The stromatolysing reagent of claim 1 which includes the following three ingredients in approximately the concentrations indicated:
  1. Tetradecyltrimethylammonium bromide: 20 g/L
  2. Dodecyltrimethylammonium chloride: 10 g/L
  3. Polyoxyethylated alkylphenol: 8 mL/L.

13. The stromatolysing reagent of claim 1 which includes the following three ingredients in approximately the concentrations indicated:
  1. Tetradecyltrimethylammonium bromide: 13 g/L
  2. Dodecyltrimethylammonium chloride: 70 g/L
  3. Polyethylene glycol p-isoalkylphenyl ether or polyoxyethylated alkylphenol: 8 mL/L.

14. The stromatolysing reagent of claim 1 which includes the following three ingredients in approximately the concentrations indicated:
  1. Tetradecyltrimethylammonium bromide: 13 g/L
  2. Dodecyltrimethylammonium chloride: 35 g/L
  3. Sodium lauryl sulfate: 1.25 g/L.

15. A stromatolysing reagent according to claim 1 for use in the measurements of two populations of leukocytes.

16. A stromatolysing reagent according to claim 1 for use in the measurements of three populations of leukocytes.

17. The stromatolysing reagent of claim 1 for the measurements of three populations of leukocytes, stromatolysing reagent including the following three ingredients in approximately the concentrations indicated:
  1. Tetradecyltrimethylammonium bromide: 6.5 g/L
  2. Dodecyltrimethylammonium chloride: 18.8 g/L
  3. Polyoxyethylated alkylphenol: 3 mL/L.

18. In a method for determination of at least two leukocyte populations in blood which is being processed through a blood cell analyzer using the Coulter Principle of operation which includes the step of:
  I. diluting a blood sample with an electronically conductive isotonically balanced diluent, the improvement which comprises the step of:
  II. stromatolysing with a reagent comprising an aqueous solution of at least two quaternary ammonium salts having surface active properties, and an additive which contains at least one non-cationic surfactant, said salts and additive being present in sufficient amounts for affecting the normal leukocyte volume distributions during said stromatolysation so as to cause the volume distribution measurements of said blood cell analyzer to lie within predetermined limits, with reference to at least one volume reference point.

19. The method of claim 18 in which the diluent comprises an aqueous solution of:
  1. buffering means,
  2. cell membrane stabilizing means,
  3. germicidal means, and
  4. means for producing an osmotically balanced and substantially neutral pH solution.

20. The method of claim 18 in which the diluent comprises an aqueous solution of:
  1. Procaine hydrochloride,
  2. N-(2-acetamido)iminodiacetic acid (ADA),
  3. Dimethylolurea, and
  4. Alkali metal sulfate and alkali metal halide, said diluent being an osmotically balanced and substantially neutral pH solution; and said stromatolysing reagent further comprises an alkali metal cyanide; and said ingredients are present in a concentration range which is effective to enable the differential determination of leukocyte populations and hemogram values.

21. The method of claim 18 wherein said quaternary ammonium salts are selected from the group consisting of:
  1. Dodecyltrimethylammonium chloride,
  2. Tetradecyltrimethylammonium bromide, and
  3. Hexadecyltrimethylammonium bromide.

22. The method of claim 18 wherein said non-cationic surfactant additive is selected from the group consisting of:
  1. Polyoxyethylated alkylphenols, 2. Poly(oxypropylene)poly(oxyethylene)condensates,
3. Polyethylene glycol p-isoalkylphenyl ethers, and
4. An alkali metal salt of a $C_{10}$–$C_{18}$ alkyl sulfate.

23. In a method for the size differentiation of at least two populations of leukocytes in blood, the blood being processed through a blood cell analyzer using the Coulter Principle of operation which employs a leukocyte sensing zone, the blood having been first diluted with an electrically conductive isotonically balanced diluent, the improvement wherein said stromatolysing reagent comprises an aqueous solution of at least two quaternary ammonium salts having surface active properties and an additive which is at least one non-cationic surfactant, said salts and additive being present in sufficient amounts for positioning said leukocyte populations relative to one another and relative to a blood cell volume reference point, within the time constraints of said blood cell analyzer.

24. In the method of claim 23 the improvement wherein said quaternary ammonium salts have the formula

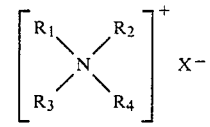

where $R_1$ is a long chain alkyl radical having 10 to 18 carbon atoms, $R_2$, $R_3$, $R_4$ are short chain alkyl radicals having 1 to 6 carbon atoms and $X^-$ is a salt forming radical such as $Cl^-$, $Br^-$, $PO_4^{3-}$ and $CH_3PO_4$.

* * * * *